July 5, 1966 D. L. ARMSTRONG ETAL Plant Pat. 2,653
ROSE PLANT
Filed Aug. 17, 1965
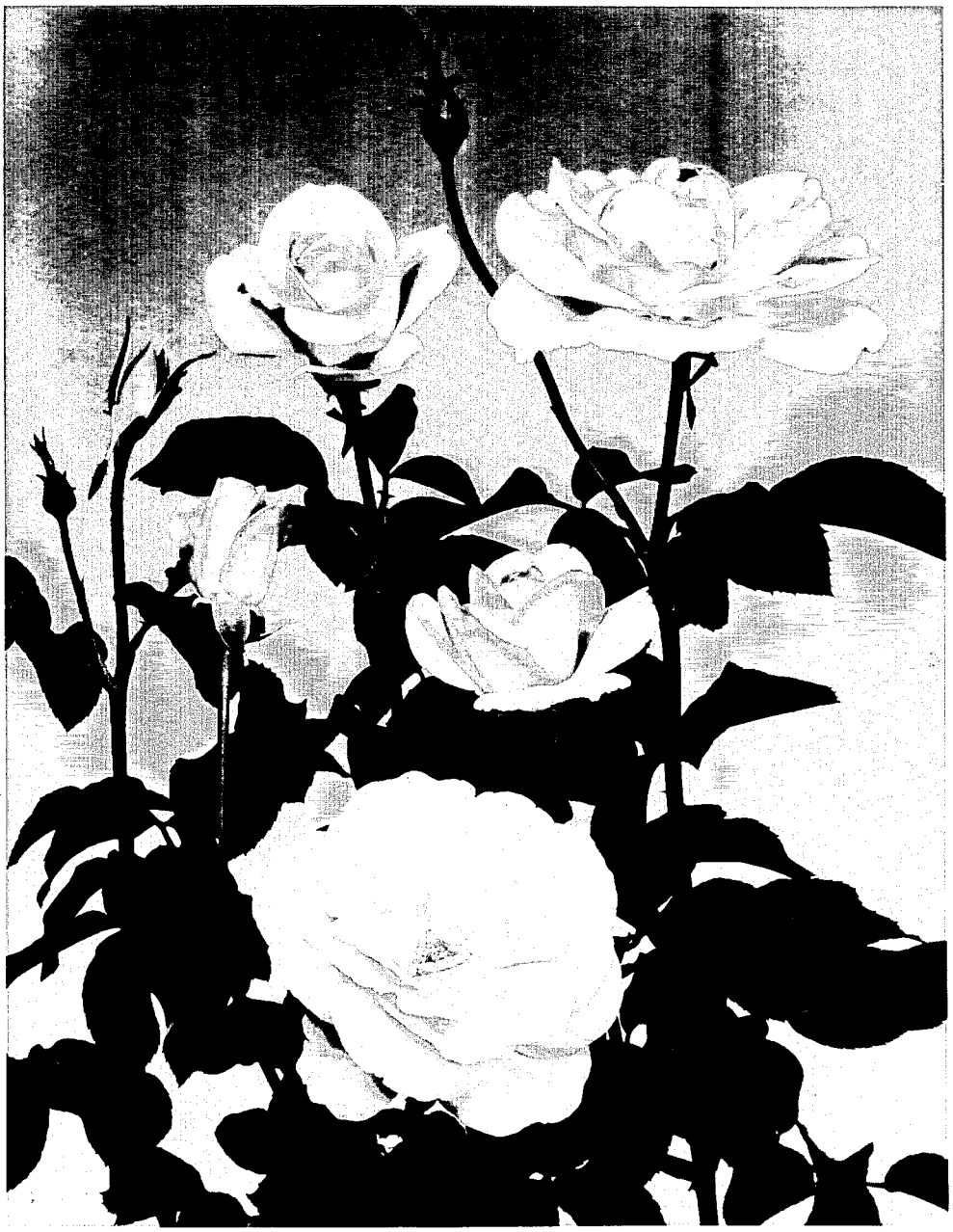
Inventors.
D. L. Armstrong
H. C. Swim
By: Robb & Robb
Attorneys.

United States Patent Office

Plant Pat. 2,653
Patented July 5, 1966

2,653
ROSE PLANT

David L. Armstrong and Herbert C. Swim, Ontario, Calif., assignors to Armstrong Nurseries, Inc., Ontario, Calif., a corporation of California Filed Aug. 17, 1965, Ser. No. 480,536
1 Claim. (Cl. Plt.—18)

The present invention relates to a new and distinct variety of rose plant of the hybrid tea class, which was originated by us by crossing the variety known as "Fandango" (Plant Patent No. 894) with an unnamed variety which is the subject of Plant Patent No. 1,277, the variety "Fandango" being the seed parent and the unnamed variety being the pollen parent.

The general objective of this breeding was to produce a new and improved rose variety which bears flowers whose color falls in the pink or light red color range and of the hybrid tea or grandiflora type, combined with the large flower size, good bud form and large, glossy, disease resistant foliage characteristic of the seed parent, along with the floriferousness, excellent, dense, bushy habit, and vigor that are characteristic of the unnamed pollen parent.

This objective was fully achieved, along with other desirable improvements, as evidenced by the following characteristics which are outstanding in the new variety and which distinguish it from its parents, as well as from all other varieties of which we are aware:

(1) An upright-spreading habit, with a vigor considerably greater than that of the average hybrid tea rose variety;

(2) Attractive, dark green, medium to large, semi-glossy, disease resistant foliage;

(3) A very floriferous habit with the flowers often borne singly, but also often borne in small clusters on the most vigorous shoots and bottom breaks;

(4) An excellent urn-shaped bud form and attractive and graceful open flower form, with the flower being moderately double and of medium size; and (5) A distinctive and attractive general color tonality of the flowers ranging between Phlox Pink and Fuchsine Pink, but becoming lighter with age.

In comparison with its seed parent "Fandango," the new variety is considerably more vigorous, tends to bear flowers in clusters on the more vigorous shoots rather than usually singly as in the case of "Fandango," the flowers of new variety have considerably more petals, and the flower color is pink, as distinguished from the cherry red flowers of "Fandango."

As compared with its unnamed pollent parent, the flowers of the new variety are considerably larger in size, and the flowers are often borne singly, as well as in small clusters, whereas those of the pollen parent usually are borne in clusters only and the clusters are larger.

Asexual reproduction of our new variety by budding, as performed at Ontario, California, shows that the foregoing characteristics and distinctions come true to form and are established and transmitted through succeeding propagations.

The accompanying drawings shows typical specimens of the vegetative growth and flowers of our new variety in different stages of development, with some of the flowers and vegetative growth being depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W)) and Robert Ridgway's Color Standards and Nomenclature (hereinafter abbreviated as (R)), as indicated:

Type: Tall; bush; outdoors; seedling; for cut flowers and for garden decoration.
Class: Hybrid tea.
Breeding: Seedling.
*Seed parent.*—"Fandango."
*Pollen parent.*—An unnamed variety which is the subject of Plant Patent No. 1,277.
Propagation: Holds its distinguishing characteristics through succeeding propagations by budding.

*Flower*

Locality where grown and observed: Ontario, California.
Flowers borne: Sometimes singly and sometimes from 3 to 5 or more to stem; in irregular clusters; on stems of normal strength and medium length.
Quantity of bloom: Abundant, outdoors.
Continuity: Nearly continuous during growing season.
Frangrance: Slight.
Bud:
*Peduncle.*—Average length; from slender to average caliper; erect; usually smooth; with several to many small stipitate glands and none to few small prickles. Color—near Apple Green, Plate XVII (R), overlaid with near Prussian Red, Plate XXVII (R) on side exposed to the sun.
*Before calyx breaks.*—Size—small. Form—from short to medium length; pointed and ovoid.
*As calyx breaks.*—Color—near Spinel Red, Plate 0023, page 189 (W).
*Sepals.*—Inner surface—with fine, wooly tomentum. Outer surface—usually smooth and with none to few small stipitate glands. Alternate margins—lined with fine, wooly tomentum. Other margins—with several to many small stipitate glands and small slender foliaceous parts, sometimes with slender foliaceous appendages extending from ¼ to ⅓ sepal length.
*As first petal opens.*—Size—small. Form—from short to medium length; ovoid; usually urn-shaped. Color: Outside—near Phlox Pink, Plate 625/1, page 77 (W), with small area at base of petal near attachment near Uranium Green, Plate 63/2, page 63 (W); inside—near Phlox Pink, Plate 625/1, page 77 (W), with small area at base of petal near attachment near Primrose Yellow, Plate 601, page 65 (W).
*Opening.*—Opens up well; is not retarded or prevented from opening by cold, hot, wet or dry weather.
Bloom:
*Size (when fully open).*—Average; from 3½ inches to 4½ inches.
*Petalage.*—Double; from 18 to 24 petals, plus 4 to 6 petaloids; arranged irregularly.
*Form.*—High-centered at first, but becoming flat to cupped; petals being at first tightly cupped, with tips rolled outward, but later becoming more loosely flat to cupped with tips rolled outward at maturity.
Petals:
*Texture.*—Medium thickness; moderately leathery.
*Appearance.*—Inside—satiny. Outside—satiny.
*Shape.*—Outside—broadly obovate, with apex flat and sometimes with one or two notches. Intermediate—obovate, with apex rounded and sometimes with one or two notches. Inside—narrowly obovate and irregularly shaped, with apex rounded and with one or two notches.

This description of a newly opened flower was made from a rose grown outdoors during the month of September at Ontario, California:

*Color.*—Outer petal: Outside surface—between Phlox Pink, Plate 625/3, page 77 (W) and Fuchsine Pink, Plate 627/3, page 78 (W), with small area at base of petal near attachment near Uranium Green, Plate 63/3, page 63 (W); inside surface—between Phlox Pink, Plate 625/3, page 77 (W) and Fuchsine Pink, Plate 627/3, page 78 (W), with small area at base of petal near attachment near Uranium Green, Plate 63/2, page 63 (W). Intermediate petal: Outside surface—near Phlox Pink, Plate 625/2, page 77 (W), with small area at base of petal near attachment near Dresden Yellow, Plate 64/2, page 64 (W); inside surface—near Phlox Pink, Plate 625/2, page 77 (W), with small area at base of petal near attachment near Empire Yellow, Plate 603, page 66 (W). Inner petal: Outside surface—near Phlox Pink, Plate 625/1, page 77 (W), with small area at base of petal near attachment near Dresden Yellow, Plate 64/1, page 64 (W); inside surface—near Phlox Pink, Plate 625/1, page 77 (W), with small area at base of petal near attachment near Empire Yellow, Plate 603, page 66 (W).

This description was made from a rose that was open for three days outdoors during the month of September at Ontario, California:

*Color.*—Outer petal: Outside surface—between Rhodamine Pink, Plate 527/2, page 138 (W) and Amaranth Rose, Plate 530/2, page 139 (W), with area at base of petal near Primrose Yellow, Plate 601/3, page 65 (W); inside surface—between Dawn Pink, Plate 523/3, page 137 (W) and Rhodamine Pink, Plate 527/3, page 138 (W) with area at base of petal near Primrose Yellow, Plate 601/3, page 65 (W). Inner petal: Outside surface—near Rhodamine Pink, Plate 527/1, page 138 (W) with small area at base near attachment near Primrose Yellow, Plate 601/2, page 65 (W); inside surface—near Rhodamine Pink, Plate 527/2, page 138 (W), with small area at base near Primrose Yellow, Plate 601/2, page 65 (W).

*General color effect.*—Newly opened flower—between Phlox Pink, Plate 625/1, page 77 (W) and Fuchsine Pink, Plate 627/3, page 78 (W). 3-days open—between Dawn Pink, Plate 523/3, page 137 (W) and Rhodamine Pink, Plate 527/2, page 138 (W).

*Behavior.*—Drop off cleanly; not particularly affected by cold, hot, wet or dry weather.

*Flower longevity.*—On bush in garden—4 or 5 days during August. Cut roses grown outdoors and kept at living-room temperatures—3 or 5 days in August.

*Reproductive organs*

Stamens: Average number; arranged regularly about pistils; a few mixed with petaloids.

Filaments: From medium length to long (6 mm. to 15 mm.); most with anthers. Color—near Aureolin, Plate 3/2, page 3 (W).

Anthers: Small; all open approximately at once. Color: Upper side—margins near Chinese Yellow, Plate 606/1, page 68 (W) with remainder near Aureolin, Plate 3/2, page 3 (W); under side—margins near Chinese Yellow, Plate 606/1, page 68 (W) with remainder near Aureolin, Plate 3/2, page 3 (W).

Pollen: From sparse to moderate quantity. Color—near Tangerine Orange, Plate 9, page 9 (W).

Pistils: From average number to many (approximately 80).

Styles: Uneven; from short to average length; from thin to average caliper; bunched. Color—upper ⅔ of style near Geranium Lake, Plate 20, page 20 (W) with remainder near Empire Yellow, Plate 603/1, page 66 (W).

Stigma: Color—near Orange Buff, Plate 507/2, page 133 (W).

Ovaries: Usually all enclosed in calyx.

Hips: From short to average length; between ovoid and globulars; smooth; walls thick and fleshy. Color (half mature)—near Rainette Green, Plate XXXI (R).

Sepals: Falling soon; medium length; straight. Color: Inside—near Vetiver Green, Plate XLVII (R); outside—near Absinthe Green, Plate XXXI (R).

Seeds: From few to average number (from 30 to 40); from small to medium size.

*Plant*

Foliage:

*Leaves.*—Compound of usually 3–7 leaflets; from normal to abundant quantity; from medium to large size; leathery; semi-glossy.

*Leaflets.*—Shape—oval, with apex acute. Base—round. Margin—simply serrate.

*Color.*—Mature: Upper surface—near Forest Green, Plate XVII (R); under surface—near Chromium Green, Plate XXXII (R). Young: Upper surface—near Deep Dull Yellow-Green (1), Plate XXXII (R); under surface—near Biscay Green, Plate XVII (R), overlaid with near Prussian Red, Plate XXVII (R).

*Rachis (the supporting stem of the compound leaf).*—Average size. Upper side—grooved, with several to many small stipitate glands on edges. Under side—smooth; with few to several small stipitate glands and none to few small prickles, and with few to several small stipitate glands also on sides of rachis.

*Stipules.*—Short; moderately narrow; with short points turning out at an angle of more than 45°.

*Disease resistance.*—Better than average resistance to mildew, as compared with other varieties grown under comparable cultural conditions at Ontario, California.

Growth:

*Habit.*—Upright-spreading; much branched.

*Growth.*—Vigorous.

*Canes.*—From medium caliper to heavy.

*Main stems.*—Color—near Deep Grape Green, Plate XLI (R). Large prickles—from several to many; short; hooked slightly downward; with short, moderately broad base; color—near Light Mouse Gray, Plate LI (R). Small prickles—from few to several; color—near Light Mouse Gray, Plate LI (R). Hairs—none.

*Branches.*—Color—near Grape Green, Plate XLI (R). Large prickles—from several to many; short; hooked slightly downward; with short, moderately broad base; color—near Mikado Brown, Plate XXIX (R). Small prickles—from several to many; color—near Mikado Brown, Plate XXIX (R). Hairs—none.

*New shoots.*—Color—near Kildare Green, Plate XXXI (R), overlaid with near Prussian Red, Plate XXVII (R) on side exposed to the sun. Large prickles—few; short; hooked slightly downward; with short, broad base; color—near Mineral Red, Plate XXVII (R). Small prickles—from few to several; color—near Mineral Red, Plate XXVII (R). Hairs—none.

We claim:

A new and distinct variety of rose plant of the hybrid tea class, substantially as herein shown and described, characterized particularly as to novelty by the unique combination of an upright-spreading habit, with a vigor considerably greater than that of the average hybrid tea rose variety, attractive, dark green, medium to large, semi-glossy, disease resistant foliage, a very floriferous habit with the flowers often borne singly, but also often borne in small clusters on the most vigorous shoots and bottom breaks, an excellent urn-shaped bud form an attractive and graceful open flower form, with the flowers being moderately double and of medium size, and a distinctive and attractive general color tonality of the flowers ranging between Phlox Pink and Fuchsine Pink, but becoming lighter with age.

No references cited.

ABRAHAM G. STONE, *Primary Examiner.*

R. E. BAGWILL, *Assistant Examiner.*